(12) United States Patent
Rutter

(10) Patent No.: US 7,240,676 B2
(45) Date of Patent: Jul. 10, 2007

(54) TRACHEOTOMY VALVE UNIT

(75) Inventor: Michael John Rutter, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 246 days.

(21) Appl. No.: 10/736,266

(22) Filed: Dec. 15, 2003

(65) Prior Publication Data

US 2004/0123868 A1    Jul. 1, 2004

Related U.S. Application Data

(60) Provisional application No. 60/433,735, filed on Dec. 16, 2002.

(51) Int. Cl.
| A62B 9/04 | (2006.01) |
| A62B 9/02 | (2006.01) |
| F16K 17/26 | (2006.01) |

(52) U.S. Cl. ............... 128/207.16; 128/205.24; 128/202.27; 137/493.9

(58) Field of Classification Search ........... 128/207.14, 128/200.26, 207.16, 200.24, 203.11, 205.24, 128/201.19, 202.27, 204.26, 205.25, 206.15, 128/207.12, 207.15, 202.28, 202.29; 137/845, 137/493.9, 860, 859

See application file for complete search history.

(56) References Cited

U.S. PATENT DOCUMENTS

| 3,924,637 A | 12/1975 | Swanson |
| 4,040,428 A | 8/1977 | Clifford |
| 4,280,492 A | 7/1981 | Latham |
| 4,325,366 A | 4/1982 | Tabor |
| 4,326,507 A * | 4/1982 | Barkalow ................. 601/106 |
| 4,439,872 A | 4/1984 | Henley-Cohn et al. |
| 4,459,984 A | 7/1984 | Liegner |
| 4,494,252 A * | 1/1985 | Chaoui ......................... 623/9 |

(Continued)

FOREIGN PATENT DOCUMENTS

EP    0078685 A1    5/1983

OTHER PUBLICATIONS

Passy-Muir Communication Products—Clinical Benefits, "Clinical Benefits of the Passy-Muir Speaking Vlaves", 4 pages, http://www.passy-muir.com/clinicalbenefits.htm (Jun. 21, 2002).

(Continued)

Primary Examiner—Justine R. Yu
Assistant Examiner—Annette Dixon
(74) Attorney, Agent, or Firm—Ronald J. Richter; Donald E. Hasse; Hasse & Nesbitt LLC

(57) ABSTRACT

A tracheotomy valve unit for use with a tracheotomy tube inserted into a patient's trachea comprises a first end for connection to the tracheotomy tube, a second end comprising a valve unit inlet, a first valve that permits airflow to the tube when the patient inhales and blocks airflow from the tube when the patient exhales thereby permitting speech, and a second valve that permits airflow from the tube back out the valve unit when the intrathoracic pressure during expiration is greater than about 12 cm of water. The second valve functions as a pressure release valve that increases tolerance and wearing comfort. In one embodiment, the second valve comprises a slit valve or an umbrella valve.

15 Claims, 6 Drawing Sheets

U.S. PATENT DOCUMENTS

| | | | |
|---|---|---|---|
| 4,538,607 A | | 9/1985 | Saul |
| 4,582,058 A | | 4/1986 | Depel et al. |
| 4,593,689 A | * | 6/1986 | White ................... 128/201.19 |
| 4,596,248 A | * | 6/1986 | Lieberman ............. 128/207.16 |
| 4,627,433 A | * | 12/1986 | Lieberman ............. 128/207.16 |
| 4,697,593 A | * | 10/1987 | Evans et al. ................ 600/343 |
| 4,759,356 A | | 7/1988 | Muir |
| 4,763,803 A | | 8/1988 | Schneider |
| 5,201,722 A | | 4/1993 | Moorehead et al. |
| 5,392,775 A | | 2/1995 | Adkins, Jr. et al. |
| 5,411,491 A | | 5/1995 | Goldhardt et al. |
| 5,727,594 A | | 3/1998 | Choksi |
| 5,765,560 A | | 6/1998 | Verkerke et al. |
| 5,957,978 A | | 9/1999 | Blom |
| 6,024,120 A | | 2/2000 | Yam et al. |
| 6,102,245 A | | 8/2000 | Haberman |
| 6,116,457 A | | 9/2000 | Haberman |
| 6,193,751 B1 | | 2/2001 | Singer |
| 6,352,525 B1 | | 3/2002 | Wakabayashi |
| 6,409,967 B1 | | 6/2002 | McIntosh |
| 6,544,292 B1 | | 4/2003 | Laghi |
| 6,604,523 B2 | * | 8/2003 | Lurie et al. ............. 128/205.24 |
| 6,986,349 B2 | * | 1/2006 | Lurie ................... 128/202.28 |
| 2004/0089291 A1 | * | 5/2004 | Persson ................ 128/200.16 |

OTHER PUBLICATIONS

Passy-Muir Communication Products—The Design Advantage, 2 pages, http://www.passy-muir.com/advantage.htm (Jun. 21, 2002).

Passy-Muir Technical—Positive Airflow, 1 page, http://www.passy-muir.com/positive.htm (Jun. 21, 2002).

Passy-Muir Communication Products—Valve Descriptions, "Passy-Muir Speaking Valves Product Descriptions", 5 pages, http://www.passy-muir.com/valves.htm (Aug. 1, 2002).

Passy-Muir Communication Products—The Design Difference, "The Design Difference—Positive Closure—a patented closed position "No Leak" design", 2 pages, http://www.passy-muir.com/difference.htm (Oct. 21, 2003).

Boston Medical Products, Inc., "Montgomery® Tracheostomy Speaking Valve" (1 page) and "VENTRACH™ Speaking Valve" (1 page), http://www.bosmed.com/products/tracheostomy/ (Jul. 21, 2002).

Nellcor—Critical Care Systems, Phonate™ Speaking Valves (2 pages), http://www.nellcor.com/products/Product.asp (Jul. 21, 2002).

Minivalve, "Duckbill Valves—DU 027.001 SD" (2 pages) and Umbrella Valves (UM 070.002 SD) (3 pages) http://www.minivalve.com (Nov. 21, 2003).

Rutter, Dr. Michael, Abstract and Power Point Presentation, Sentac Conference Dec. 2-5, 1999.

Rutter, Dr. Michael, Abstract and Power Point Presentation, Otolaryngology-Head and Neck Surgery Conference Sep. 9-12, 2001.

* cited by examiner

TRACHEOTOMY VALVE UNIT

CROSS-REFERENCE TO RELATED APPLICATIONS

This application claims the benefit of co-pending U.S. Provisional Application No. 60/433,735, filed Dec. 16, 2002.

BACKGROUND OF THE INVENTION

The present invention relates to a tracheotomy valve unit adapted for use with a tracheotomy tube inserted into a patient's trachea. More particularly, the invention relates to a tracheotomy valve unit containing a first valve that permits airflow through the valve unit when the patient inhales and blocks airflow through the valve unit when the patient exhales to enable speech, and a second pressure release valve that reduces intrathoracic pressure during expiration and improves comfort.

Individuals with tracheotomy tubes often have difficulty with speech, which is normally produced by airflow past the vocal cords on expiration. If a tracheotomy tube is present, air on expiration is mainly expelled through the tracheotomy tube rather than through the vocal cords. To overcome this problem, a one-way tracheotomy valve (or speaking valve) can be placed over the entrance to the tracheotomy tube. This allows air to be inhaled through the valve and into the tracheotomy tube, but does not allow exhaled air to escape back through the tracheotomy tube and out the valve. Instead, the air is forced around the tracheotomy tube, or through the shaft of the tube if it is fenestrated, and escapes through the vocal cords, permitting speech. The corresponding increase in subglottic pressure during exhalation also facilitates swallowing and cough production.

U.S. Pat. No. 4,759,356, Muir, issued Jul. 26, 1988, discloses such a one-way tracheotomy valve that prevents airflow except when the patient inhales. This is accomplished by positively biasing a flexible diaphragm against a valve seat using a rivet structure. The valve is thus entirely closed during the exhalation phase of the respiration cycle and at the beginning and end of the inhalation phase of the cycle.

U.S. Pat. No. 4,582,058, Depel et al., issued Apr. 15, 1986, discloses a tracheostoma valve assembly containing a spring-biased main valve that remains open during normal breathing and closes during normal air flow associated with speech. The valve assembly includes a separate external relief valve that is closed during normal breathing and speaking and opens to release air pressure resulting from a substantially increased air pressure within the valve assembly, such as due to a cough. The relief valve automatically closes when the air pressure is reduced in the valve assembly.

However, some people with a tracheotomy tube, particularly children, cannot tolerate a speaking valve because their airway is too obstructed by the tube to allow full and comfortable clearance of air inspired through the one-way valve. This may be caused by an upper tracheal or subglottic stenosis, suprastomal collapse, or too large a tracheotomy tube. These conditions limit the escape of inhaled air, and may result in a feeling of suffocation and raised intrathoracic pressure on expiration. This may cause the speaking valve to be displaced, or may result in chronically raised intrathoracic pressure which, in turn, may compromise venous blood return to the heart and predispose one to pulmonary hypertension.

Thus, there is a need for a tracheotomy valve unit that allows full and comfortable clearance of inspired air and prevents the build up of excess intrathoracic pressure during expiration, while maintaining sufficient pressure to allow the user to generate speech.

BRIEF DESCRIPTION OF THE INVENTION

In one aspect, this invention relates to a tracheotomy valve unit adapted to cooperate with a tracheotomy tube inserted into a patient's trachea, said valve unit comprising:
(a) a first end adapted for connection to the free end of the tracheotomy tube;
(b) a second end comprising a valve unit inlet;
(c) a first valve that permits airflow from the valve unit inlet through the valve unit and to the tube in the patient's trachea when the patient inhales, and blocks airflow from the tube through the valve unit when the patient exhales; and
(d) a second valve that permits airflow from the tube through the valve unit and out the valve unit when the intrathoracic pressure during expiration is greater than about 12 cm of water, and blocks such airflow when the intrathoracic pressure during expiration is less than about 3 cm of water.

In another aspect, this invention relates to a tracheotomy valve unit adapted to cooperate with a tracheotomy tube inserted into a patient's trachea, said valve unit comprising:
(a) a first end adapted for connection to the free end of the tracheotomy tube;
(b) a second end comprising a valve unit inlet;
(c) a first valve that permits airflow from the valve unit inlet through the valve unit and to the tube in the patient's trachea when the patient inhales, and blocks airflow from the tube through the valve unit when the patient exhales, said first valve comprising a seating ring, a thin, flexible diaphragm biased against the seating ring, thereby making positive closure contact therewith, and a rivet for connecting the diaphragm to the seating ring, the rivet having a length to bias the diaphragm against the seating ring; and
(d) a second valve that permits airflow from the tube through the valve unit and out the valve unit when the intrathoracic pressure during expiration is greater than about 12 cm of water, and blocks such airflow when the intrathoracic pressure during expiration is less than about 3 cm of water, wherein the second valve comprises a slit valve or an umbrella valve that is located in an axial bore hole of the rivet.

BRIEF DESCRIPTION OF THE DRAWINGS

The aspects and advantages of the invention will be better understood from the following detailed description, with reference to the accompanying drawings, in which.

DETAILED DESCRIPTION OF THE INVENTION

Figure 1:
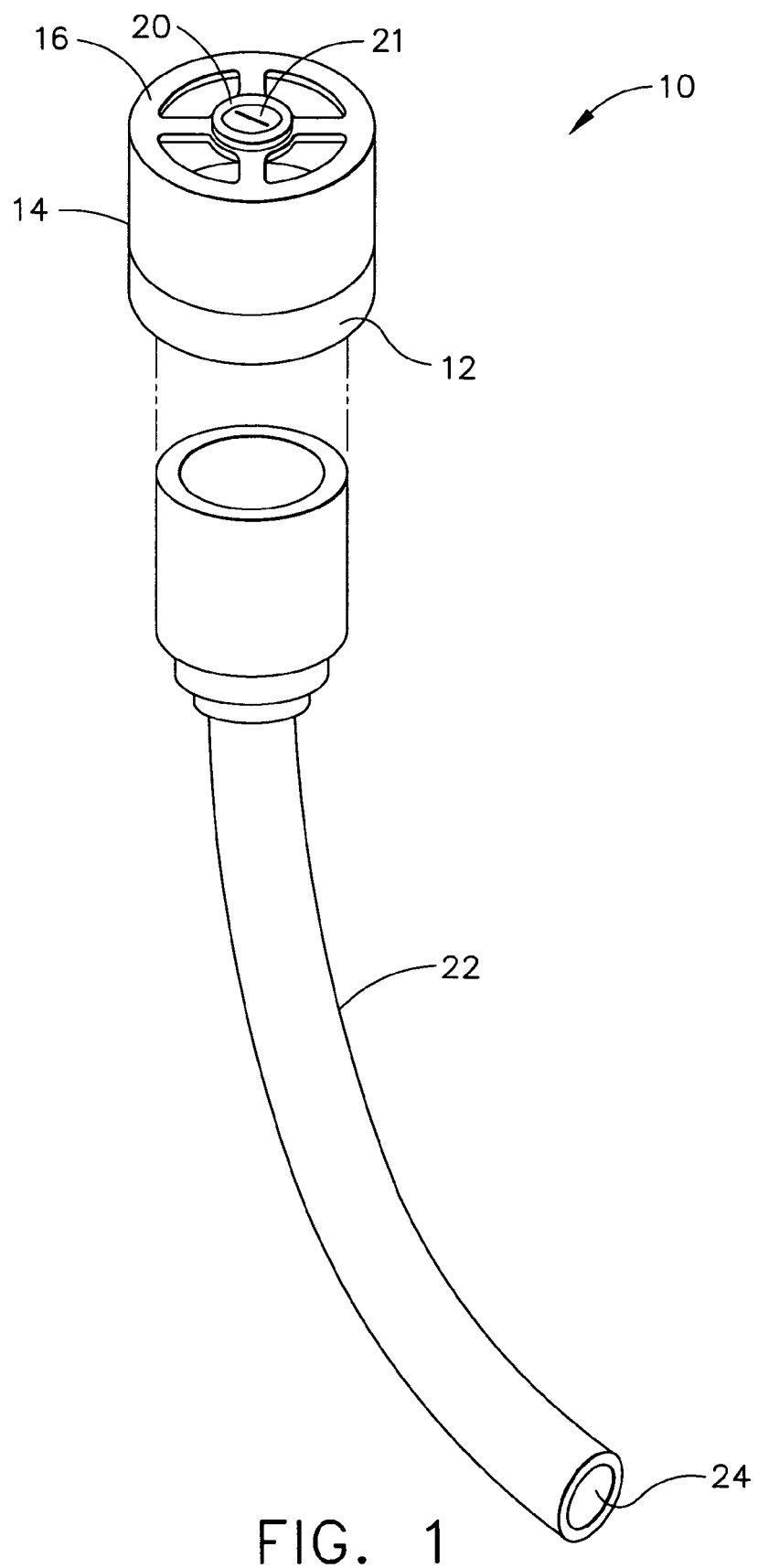
FIG. 1 is an exploded isometric view of a tracheotomy valve unit of the invention and associated tracheotomy tube assembly.

The tracheotomy valve unit of the present invention is adapted to cooperate with a tracheotomy tube inserted into a patient's trachea. The valve unit comprises a first end for connection to the free end of the tracheotomy tube; a second end comprising a valve unit inlet; a first valve that permits airflow to the tube in the patient's trachea when the patient inhales and blocks airflow from the tube through the valve unit when the patient exhales; and a second valve that permits airflow from the tube through the valve unit when the intrathoracic pressure during expiration is greater than about 12 cm of water, and blocks such airflow when the intrathoracic pressure is less than about 3 cm of water.

Tracheotomy valve units comprising such a first end, second end, and first valve suitable for use in the present invention are known in the art and described in, for example, U.S. Pat. No. 4,759,356, Muir; U.S. Pat. No. 3,924,637, Swanson; U.S. Pat. No. 4,582,058, Depel et al., and U.S. Pat. No. 5,392,775, Adkins, Jr., et al. However, these tracheotomy valve units do not contain a second valve as in the present invention, and thus may not be tolerated by people whose airway is too obstructed by the tracheotomy tube to allow full and comfortable clearance of air inspired through the first valve.

The second valve herein allows air to leak out of the valve unit in a controlled fashion during expiration to prevent the buildup of excess intrathoracic pressure. This pressure release valve typically maintains the intrathoracic pressure during expiration in the range of from about 3 to about 12 cm of water, more typically from about 4 to about 10 cm of water, for example, from about 5 to about 10 cm of water. The intrathoracic pressure during expiration may be measured on a patient by use of a portable manometer, or simulated by supplying a steady stream of airflow from an air tank through a closed tube with a valve unit of the invention attached at the end of the tube. Manometers are placed at various points in the system (before and after the valve unit) to measure the pressure and airflow flowing into and exiting the valve unit. The second valve typically opens at a pressure of about 4 cm of water, and usually is fully open at a pressure of about 12 cm of water, typically by about 10 cm of water. The second valve herein may be designed so that there is essentially no airflow through it at an intrathoracic pressure of less than about 4 cm of water, with increasing airflow, e.g., steadily increasing airflow, through it as the intrathoracic pressure increases, until maximum airflow is achieved at a pressure of about 12 cm of water, typically by about 10 cm of water. The expirational pressure during quiet breathing typically does not exceed about 10 cm of water, and is greater than about 4 cm of water, often greater than about 5 cm of water, to allow air to escape through the vocal cords with enough force to generate speech.

In one embodiment, the second valve herein comprises a slit valve such as known in the art. The slit valve may be a simple device in which the edges of the slit expand apart when internal pressure exceeds a predetermined value, to allow the pressure to decrease to a second predetermined value and the edges to once again approximate. Suitable one-way valves that may be used as or in the second valve herein are described in U.S. Pat. Nos. 6,102,245 and 6,116,457, Haberman. Other slit valves useful as or in the second valve herein are described in U.S. Pat. No. 4,439,872, Henley-Cohn et al., and U.S. Pat. No. 4,763,803, Schneider. A duckbill valve such as described in U.S. Pat. No. 5,392,775, Adkins, Jr., et al., may also be used as or in the second valve in the present invention. A two-way slit valve such as described in U.S. Pat. No. 5,201,722, Moorehead, et al., may also be used as or in the second valve, while providing an additional source of air when the patient inhales. The above patents are incorporated herein by reference.

In another embodiment, the second valve comprises an umbrella valve such as disclosed in U.S. Pat. No. 6,544,292, Laghi; U.S. Pat. No. 6,352,525, Wakabayashi; U.S. Pat. No. 6,024,120, Yam et al.; and U.S. Pat. No. 6,409,967, McIntosh; all incorporated herein by reference. A suitable umbrella valve is commercially available as UM 070.002SD from MiniValve International.

In one embodiment, the second valve is located in the center of a standard speaking valve used as or in the first valve in the present invention. For example, a standard Passy-Muir speaking valve known in the art may be fitted with a larger rivet (e.g., having a diameter of about 2.5–3 mm) that has a cylindrical bore hole through it and comprises a slit valve or an umbrella valve that functions as the second valve herein, at the inlet end of the valve unit. Alternatively, the second valve may be positioned on the side of the speaking valve used as the first valve in the present invention. A slit valve for use as the second valve herein may be made of the same or a similar material as the diaphragm of a standard speaking valve, with the thickness of the material and the length of the slit selected to provide the desired opening and closing pressure. The diaphragm of an umbrella valve is also made of a material and design selected to provide the desired opening and closing pressure.

For a better understanding of the invention, reference is now made to FIG. 1 of the drawings. FIG. 1 illustrates a tracheotomy valve unit 10 of the invention, shown in association with a tracheotomy tube assembly 22.

Figure 3:
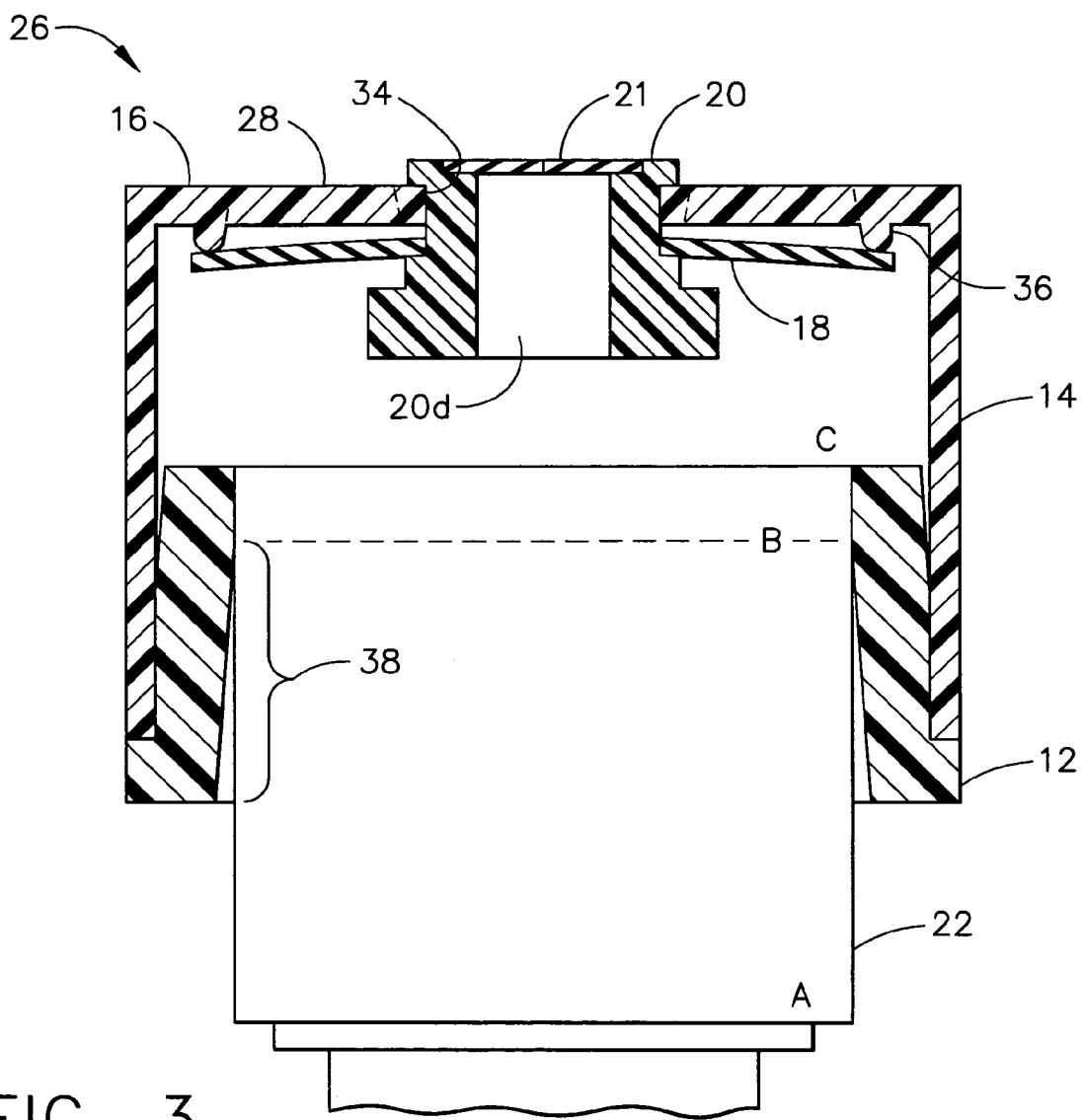
FIG. 3 is a sectional view of the valve unit, taken along the line 3—3 of FIG. 2.

In one embodiment, valve unit 10 includes a connector 12, valve base 14, support 16, diaphragm 18 (shown in FIGS. 3 and 4), and rivet 20 containing slit valve 21. FIG. 3 is a cross sectional view of the valve assembly, showing these parts. FIG. 1 is an isometric view showing these parts, except for diaphragm 18.

As shown in FIG. 1, tube assembly 22 has a tracheal end 24 that is inserted into the trachea of a patient. The other end of tube assembly 22 is removably fitted into and frictionally engages with connector 12 of valve unit 10, as shown in FIG. 3. In this embodiment, connector 12 thus represents the first end of the valve unit that is adapted for connection to the free end of the tracheotomy tube. Connector 12 is typically made of high impact plastic material, and is shown in section in FIG. 3. In one embodiment, connector 12 has an outer diameter of approximately 2.0 cm.

Connector 12 is fitted into a tubular valve base 14, as shown in FIG. 3. In one embodiment, valve base 14 is made of the same plastic material as connector 12 and the two parts are manually press fitted and bonded with a solvent such as methyl ethyl ketone. In another embodiment, the outer diameter of valve base 14 is approximately 2.1 cm, its inner diameter is approximately 2.0 cm, and it is approximately 1.7 cm high. Connector 12 typically has a slight taper to facilitate pressing it into valve base 14. (It may also have an internal taper, discussed below, to facilitate receiving the end of tracheotomy tube assembly 22.)

Figure 2:
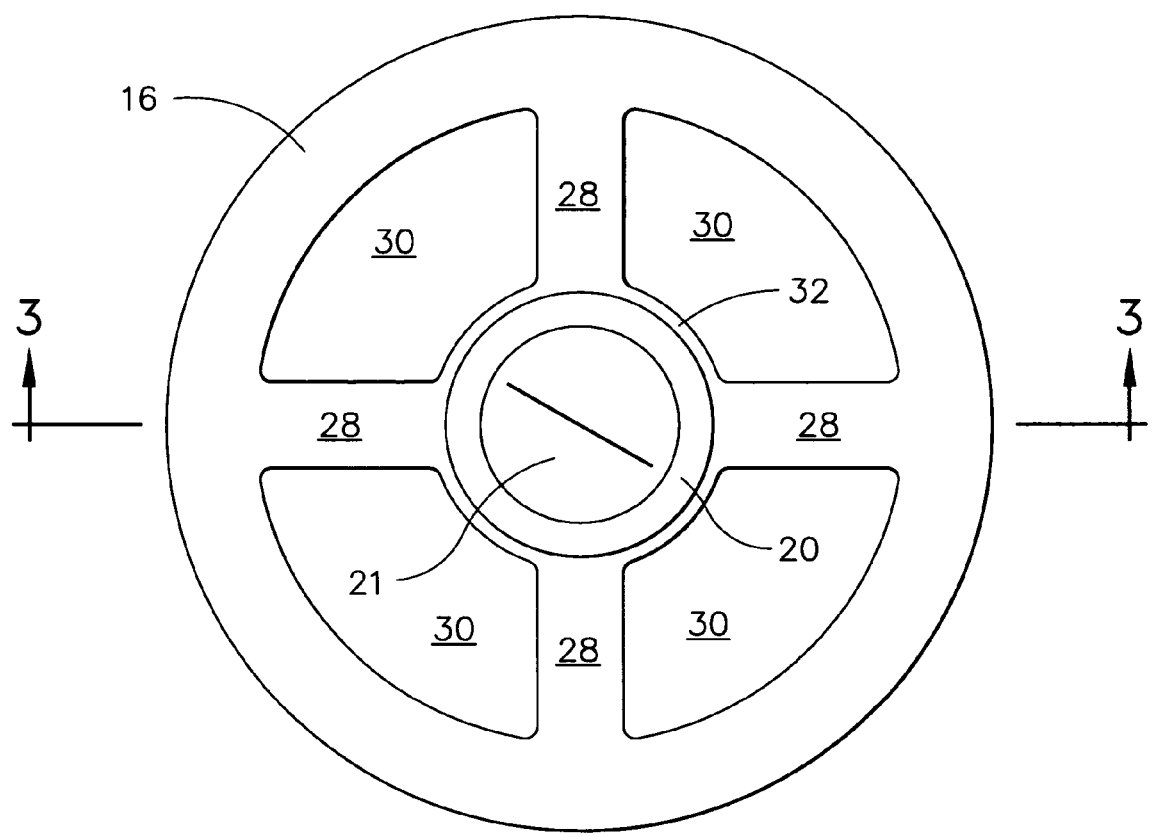
FIG. 2 is a plan view of the valve unit of FIG. 1 viewing the valve unit from the side toward the ambient air (i.e., external to the patient using the device).

FIG. 2 shows a plan view of valve unit 10 viewing it from the external end 26 of valve base 14, i.e., the end that is opposite to tracheotomy tube assembly 22. (External end 26 may also hereinafter be referred to as the proximal end of valve base 14.) This is the viewpoint taken along the arrow associated with the number 26 in FIGS. 3 and 4. External end 26 of valve base 14 comprises support 16, which is a ring-shaped member with a four-armed crosspiece 28 dividing the interior of external end 26 into four air ports 30. In this embodiment, external end 26 thus represents the second end of valve unit 10, and comprises a valve unit inlet comprising air ports 30. Crosspiece 28 has a disk-shaped member 32 at the center, through which an axial hole 34 (shown in FIG. 3) passes. Rivet 20 passes through this axial hole. Rivet 20 comprises a cylindrical axial bore hole 20d (shown in FIG. 3) and slit valve 21 at its inlet end. (Rivet 20 and slit valve 21 are shown in exaggerated size in FIGS. 2, 3 and 4 for clarity.) Support 16 is in effect a transverse wall of the valve base housing, extending radially inward from the inner walls thereof. In one embodiment of the invention, valve base 14 is molded to include support 16 and crosspiece 28, as well as disk-shaped member 32, as a single integral unit.

Figure 4:
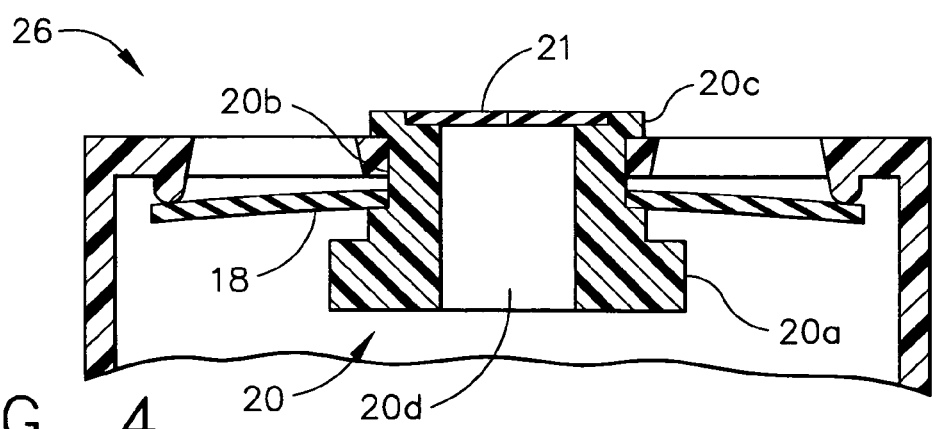
FIG. 4 is a detailed sectional view (along a different sectional line) of the portion of FIG. 3 where the bias-controlling rivet through the diaphragm is located. This figure shows the bias and curvature of the valve diaphragm in an exaggerated manner to facilitate appreciation of that feature.

As seen in FIGS. 3 and 4, support 16 has a seating ring 36 around the outer periphery of air ports 30 (shown in FIG. 2), and diaphragm 18 is pressed by rivet 20 against seating ring 36 to provide a positive closure contact and block airflow during rest (i.e., when there is neither inhalation nor exhalation), as well as during stages of inhalation when only a low opening pressure is exerted, and during exhalation.

Diaphragm 18 is connected to support 16 by rivet 20. In one embodiment, diaphragm 18 is a Silastic (i.e. a silicone elastomer) material, approximately 0.4 mm thick that is approximately 1/50 the outer diameter of the diaphragm, and it has an axial hole through which passes rivet 20. For example, the diaphragm may be a transparent, low modulus silicone sheet, such as Dow Corning Silastic, medical grade.

Rivet 20 maybe made of the same material as valve base 14 and connector 12. It is shown in FIGS. 3 and 4 compressed into its final configuration. In one embodiment, rivet 20 has a head 20a and a shank 20b approximately 3 mm in length when initially inserted through the axial hole of the diaphragm and the axial hole 34 of supporting disk-shaped member 32, and before compression. After compression, part of shank 20b has "mushroomed" into staked end 20c. (Head 20a is not changed.) Rivet 20 also has a cylindrical axial bore hole 20d extending completely through its head 20a, shank 20b and staked end 20c. Rivet 20 contains slit valve 21 at its inlet end, in staked end 20c. In one embodiment, slit valve 21 is made of a similar material to diaphragm 18, for example, a transparent, low modulus silicone, such as Dow Corning Silastic, medical grade. In one aspect, slit valve 21 has a diameter of about 1.5 mm and a thickness of about 0.1 mm. Its slit is about 1.2 mm long.

In one embodiment of the invention, diaphragm 18 is biased closed in the following manner. As shown in FIGS. 3 and 4, support 16 has a raised seating ring 36 on its inner face. Diaphragm 18 is initially fastened to the crosspiece with an axial, longitudinally disposed, "floating rivet". This permits the diaphragm initially to "float" longitudinally on the rivet, i.e., axially within valve base 14. The rivet is compressed to bias the diaphragm against seating ring 36, which is slightly raised toward the diaphragm with respect to the inner surface of crosspiece 28. The more the rivet is compressed, the more firmly the diaphragm is pulled up against the valve seat. This in turn biases the diaphragm more strongly against leakage airflow at the beginning of exhalation.

In another embodiment, seating ring 36 is raised approximately 0.4 mm from the inner face of support 16. As shown in FIGS. 3 and 4, the bottom of seating ring 36 extends below the bottom surface of the rest of support 16, such as the bottom of crosspiece 28, by a distance that is approximately 0.4 mm. Thus, if rivet 20 is given about 0.2 mm of end play after compression, it preloads diaphragm 18 approximately 0.2 mm toward seating ring 36. (As shown in FIG. 3, if the air gap between the top of diaphragm 18 and the bottom of crosspiece 28 of support 16 is about 0.2 mm, then about 0.2 mm of the thickness of diaphragm 18 (which is about 0.4 mm thick) will have to be moved up above the bottom of seating ring 36 and into the space enclosed within the seating ring. This occurs because the distance between the bottom of crosspiece 28 and the bottom of seating ring 36 is about 0.4 mm). That is, considering the "central portion" of diaphragm 18 to be that portion thereof immediately surrounding rivet 20, as shown in FIG. 4, the upper part of the central portion of diaphragm 18 is pressed into the lower part of the space surrounded by the bottom of seating ring 36. Approximately half of the thickness of diaphragm 18 is above an imaginary plane laterally extending across the very bottom of seating ring 36, and approximately half of said thickness is therebelow. As shown in FIG. 4, however, the amount of extension of diaphragm 18 into said space is slightly exaggerated, in order to make it easier to visualize the structure. This amount of preloading results in a bias equivalent to approximately 8 to 15 mm of water head, with the about 0.4 mm Silastic diaphragm described above, and makes diaphragm 18 seat completely against seating ring 36. This produces an effective closure that maintains a positive, uninterrupted contact all along the seating ring.

The effective length of rivet 20 is established during installation by blocking head 20a of the rivet with an adjustable support while at the same time heat-staking end 20c. Adjustment of the adjustable support then compresses rivet 20 and forms heat-staked end 20c, which mounts the diaphragm to support 16 and preloads diaphragm 18. A staking machine may be designed for this purpose using conventional technology with the heat selected at about 177 degrees Celsius to within 10 degrees. Slit valve 21 may then be inserted in the inlet end of rivet 20, covering axial bore hole 20d.

Returning to FIG. 3, it is seen that connector 12 has a coupling section 38 for frictionally engaging tracheotomy tube assembly 22. In one embodiment, section 38 is tapered so that it can be placed onto tracheotomy tubes with standard 15 mm hubs and of diameters ranging from about 14.9 to 15.4 mm. This is accomplished by having an entrance tapered from an initial inner diameter of about 15.5 mm at point A until the taper intersects a cylindrical bore of approximately 15.3 mm at point B, and then the cylindrical bore continues until point C. This permits enough room for compression of the tracheotomy tube and expansion of the housing to provide a snug frictional fit for various tracheotomy tubes, without interfering with the valve unit at the externally directed end. This feature permits universal fit of the valve unit onto standard tracheotomy tubes, so that the invention is not restricted to use with any particular type of tracheotomy tube. The invention may also be used with in-line respirators, increasing tolerance and comfort while permitting speech.

During use, the tracheal end 24 of tracheotomy tube assembly 22 is inserted through the tracheotomy neck opening below the patient's larynx and extends to the patient's trachea. As described above, the tracheotomy valve unit 10 is removably mounted on the free end of tube assembly 22. When the patient inhales, diaphragm 18 opens and allows air to flow through air ports 30. The first valve thus permits airflow from the valve unit inlet through the valve unit and to the tube in the patient's trachea. When the patient exhales, diaphragm 18 closes and the first valve blocks airflow from the tube through the valve unit to the atmosphere. Airflow is instead redirected upward in the direction of the larynx and epiglottis, toward the sinuses and mouth, permitting speech. However, when the intrathoracic pressure during expiration is greater than about 12 cm of water, the second valve (in this case slit valve 21) is open and permits airflow from tracheotomy tube assembly 22 back through valve unit 10 and out the valve unit inlet. In one embodiment, slit valve 21 begins to open when the intrathoracic pressure during expiration reaches about 4 cm of water, and is fully open when the intrathoracic pressure reaches about 10 cm of water. The valve unit of the invention thus improves comfort and allows some people to tolerate a speaking valve who could not otherwise do so because their airway is too obstructed to comfortably clear air inspired through the first valve.

Figure 5:
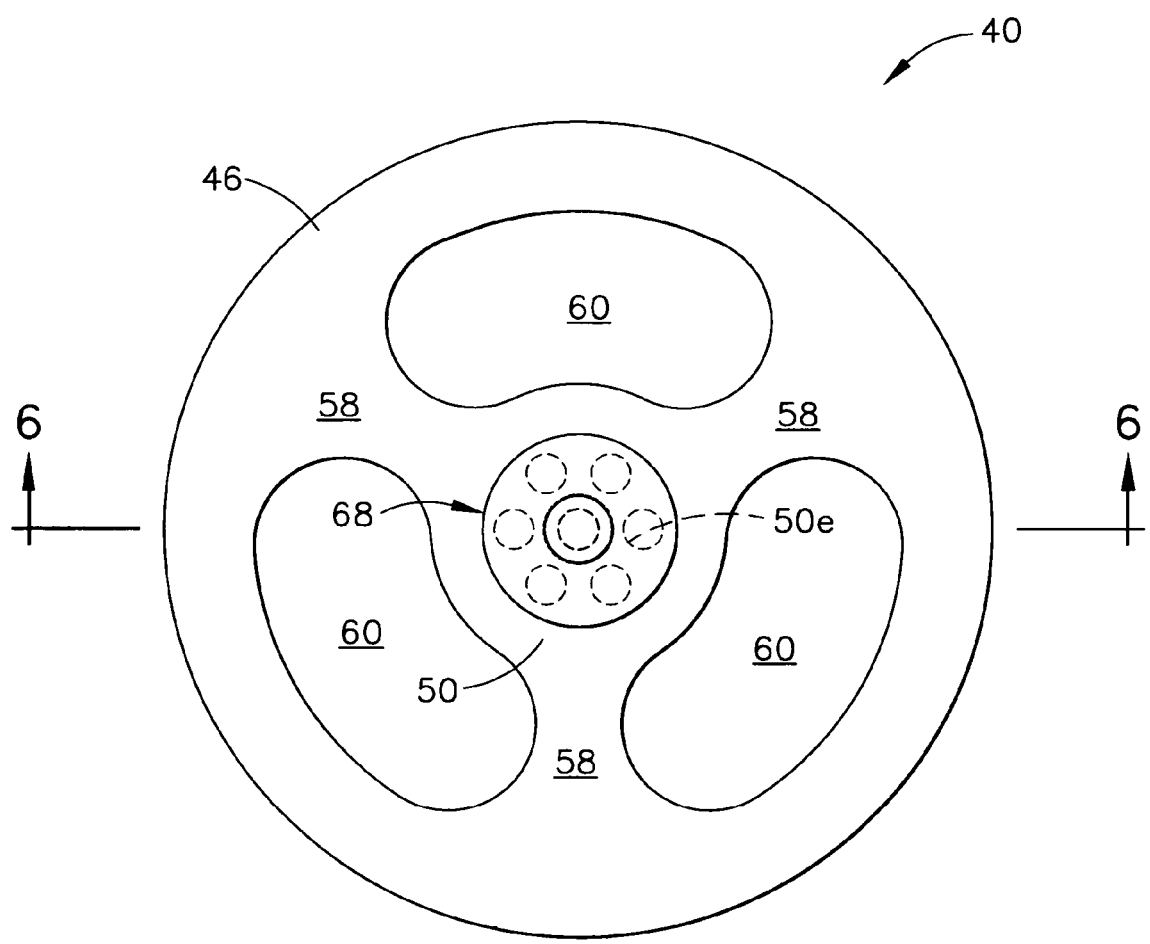
FIG. 5 is a plan view of an alternative tracheotomy valve unit of the invention viewing the valve unit from the side toward the ambient air (i.e., external to the patient using the device).
Figure 6:
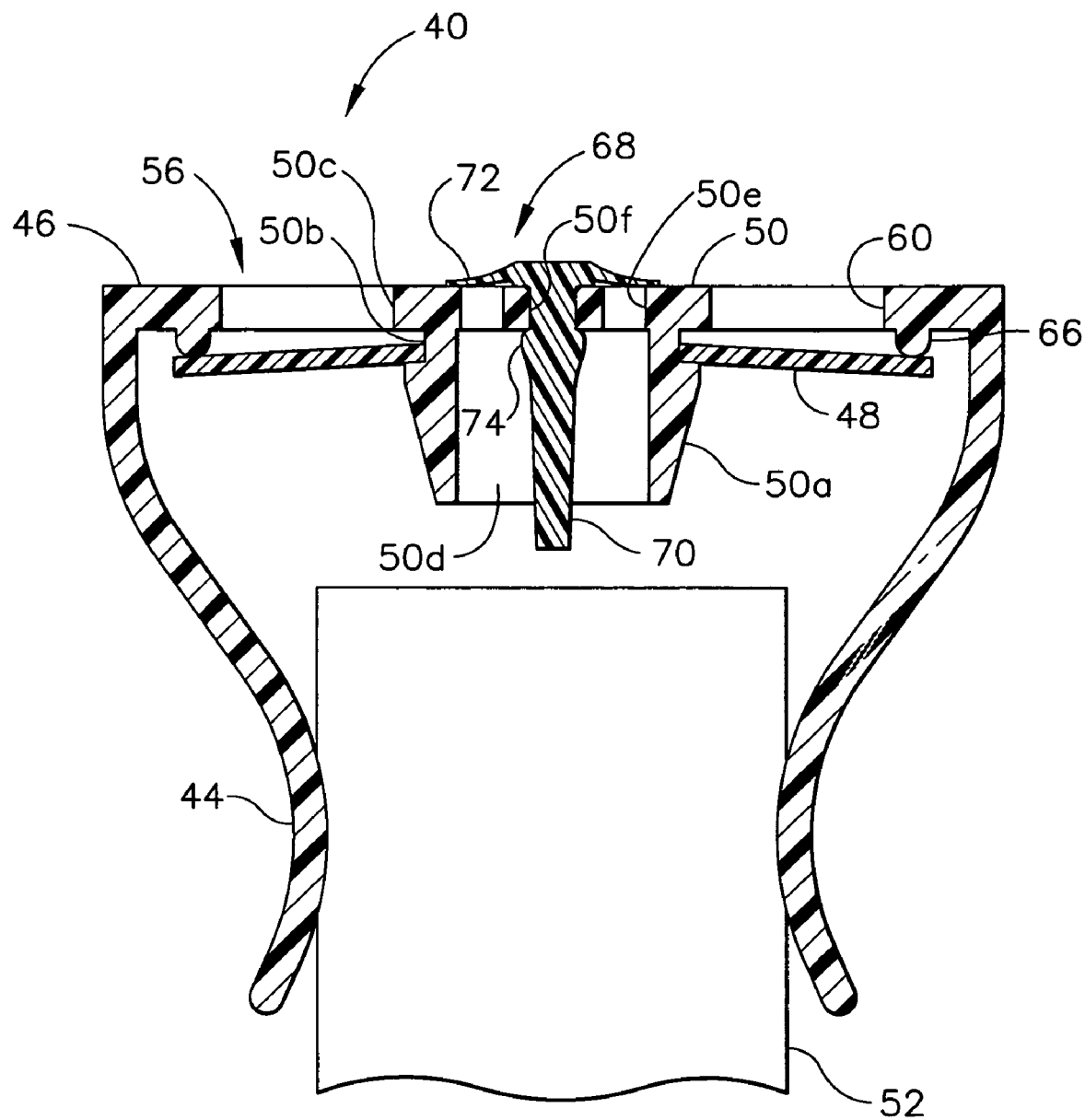
FIG. 6 is a sectional view of the valve unit of FIG. 5, taken along the line 6—6.

FIG. 5 is a plan view of an alternative valve unit 40 viewing it from the external end 56 of valve base 44 (shown is FIG. 6), i.e., the end that is opposite to the tracheotomy tube assembly. This is the viewpoint taken along the arrow associated with the number 56 in FIG. 6. Valve unit 40 comprises a valve base 44 (shown in FIG. 6), support 46, diaphragm 48 (shown in FIG. 6), and rivet 50 comprising umbrella valve 68. FIG. 6 is a cross sectional view of the valve assembly, showing these parts and tube assembly 52. The distal end of tube assembly 52 is removably fitted into and frictionally engages with valve base 44, as shown in FIG. 6. Valve base 44 is typically made of high impact plastic material. In one embodiment, valve base 44 has an outer diameter of approximately 2.0 cm where it engages the distal end of tube assembly 52. Valve base 44 typically has a slight outward taper at its end opposite support 46 to facilitate receiving the end of tube assembly 52.

External end 56 of valve base 44 comprises support 46, which is a ring-shaped member with a three-armed crosspiece 58 dividing the interior of external end 56 into three air ports 60. In this embodiment, external end 56 thus represents the second end of valve unit 40, and comprises a valve unit inlet comprising air ports 60. Crosspiece 58 is connected to rivet 50, which forms the central portion of valve unit 40. Rivet 50 comprises cylindrical axial bore hole 50d (shown in FIG. 6). Umbrella valve 68 fits in the inlet end of rivet 50. (Rivet 50 and umbrella valve 68 are shown in exaggerated size in FIGS. 5 and 6 for clarity.) Support 46 is in effect a transverse wall of the valve base housing, extending radially inward from the inner walls thereof. In one embodiment of the invention, valve base 44 is molded to include support 46, crosspiece 58, and rivet 50 as a single integral unit.

As seen in FIG. 6, support 46 has a seating ring 66 around the outer periphery of air ports 60, and diaphragm 48 is pressed by rivet 50 against seating ring 66 to provide a positive closure contact and block airflow during rest (i.e., when there is neither inhalation nor exhalation), as well as during stages of inhalation when only a low opening pressure is exerted, and during exhalation.

Diaphragm 48 is connected to support 46 by rivet 50. In one embodiment, diaphragm 48 is a Silastic material, approximately 0.4 mm thick that is approximately 1/50 the outer diameter of the diaphragm, and it has an axial hole through which passes rivet 50. For example, the diaphragm may be a transparent, low modulus silicone sheet, such as Dow Coming Silastic, medical grade.

Rivet 50 may be made of the same material as valve base 44. In one embodiment, rivet 50 has a head 50a, and a shank 50b approximately 3 mm in length when initially formed. Rivet 50 also has an end 50c and a cylindrical axial bore hole 50d extending through its head 50a and shank 50b. End 50d comprises a plurality (e.g., six as shown in FIG. 5) of cylindrical axial bore holes 50e through which air flows when umbrella valve 68 is in an open position. End 50d also comprises a cylindrical axial bore hole 50f through which stem 70 of umbrella valve 68 passes. Umbrella valve 68 also comprises an umbrella-shaped, convex sealing diaphragm 72 that is compressed or biased against the external end of rivet 50 (i.e., the end that is opposite tube assembly 52). Diaphragm 72 extends laterally beyond and completely covers the cylindrical axial bore holes 50e when umbrella valve 68 is in a closed position, as shown in FIG. 6. In one embodiment, umbrella valve 68 is made of an elastomeric material, for example, a transparent, low modulus silicone, such as Dow Corning Silastic, medical grade. Stem 70 of umbrella valve 68 is tapered so that it can be pulled through axial bore hole 50f until the central portion of diaphragm 72 contacts the external end of rivet 50. A ridge 74 on stem 70 holds umbrella valve 68 snuggly in place and prevents it from easily being removed from rivet 50. In one embodiment, diaphragm 72 of umbrella valve 68 has a diameter of about 1.5 mm and a thickness of about 0.1 mm at its edges, and stem 70 has a length of about 5 mm and a diameter at its free end of about 2.3 mm. In another embodiment, each axial bore hole 50e and 50f has a diameter of about 1.5 mm.

In one embodiment of the invention, diaphragm 48 is biased closed in the following manner. As shown in FIG. 6, support 46 has a raised seating ring 66 on its inner face. Diaphragm 48 is initially slipped over the head 50a of rivet 50 and forced into place along shank 50b. This permits diaphragm 48 initially to "float" longitudinally on the rivet, i.e., axially within valve base 44. The rivet is compressed to bias diaphragm 48 against seating ring 66, which is slightly raised toward the diaphragm with respect to the inner surface of crosspiece 58. The more the rivet is compressed, the more firmly the diaphragm is pulled up against the valve seat. This in turn biases the diaphragm more strongly against leakage airflow at the beginning of exhalation.

In another embodiment, seating ring 66 is raised approximately 0.4 mm from the inner face of support 46. As shown in FIG. 6, the bottom of seating ring 66 extends below the bottom surface of the rest of support 46, such as the bottom of crosspiece 58, by a distance that is approximately 0.4 mm. Thus, if rivet 50 is given about 0.2 mm of end pay after compression, it preloads diaphragm 48 approximately 0.2 mm toward seating ring 66. (As shown in FIG. 6, if the air gap between the top of diaphragm 48 and the bottom of crosspiece 58 of support 46 is about 0.2 mm, then about 0.2 mm of the thickness of diaphragm 48 (which is about 0.4 mm thick) will have to be moved up above the bottom of seating ring 66 and into the space enclosed within the seating ring. This occurs because the distance between the bottom of crosspiece 58 and the bottom of seating ring 66 is about 0.4 mm). That is, considering the "central portion" of diaphragm 48 to be that portion thereof immediately surrounding rivet 50, as shown in FIG. 6, the upper part of the central portion of diaphragm 48 is pressed into the lower part of the space surrounded by the bottom of seating ring 66. Approximately half of the thickness of diaphragm 48 is above an imaginary plane laterally extending across the very bottom of seating ring 66, and approximately half of said thickness is below the plane. As shown in FIG. 6, however, the amount of extension of diaphragm 48 into said space is slightly exaggerated, in order to make it easier to visualize the structure. This amount of preloading results in a bias equivalent to approximately 8 to 15 mm of water head, with the about 0.4 mm Silastic diaphragm described above, and makes diaphragm 48 seat completely against seating ring 66. This produces an effective closure that maintains a positive, uninterrupted contact all along the seating ring.

The effective length of rivet 50 is established during installation by blocking head 50a of the rivet with an adjustable support while at the same time heat-staking end 50c. Adjustment of the adjustable support then compresses rivet 50, which mounts the diaphragm to support 46 and preloads diaphragm 48. A staking machine may be designed for this purpose using conventional technology with the heat selected at about 177 degrees Celsius to within 10 degrees. Umbrella valve 68 may then be inserted in the inlet end of axial bore hole 50f.

During use, the tracheal end of tracheotomy tube assembly 52 is inserted through the tracheotomy neck opening below the patient's larynx and extends to the patient's trachea. As described above, the tracheotomy valve unit 40 is removably mounted on the free end of tube assembly 52. When the patient inhales, diaphragm 48 opens and allows air to flow through air ports 60. The first valve thus permits airflow from the valve unit inlet through the valve unit and to the tube in the patient's trachea. During inhalation, diaphragm 72 flattens out against the external end of rivet 50, preventing air from flowing through umbrella valve 68. When the patient exhales, diaphragm 48 closes and the first valve blocks airflow from the tube through the valve unit to the atmosphere. Airflow is instead redirected upward in the direction of the larynx and epiglottis, toward the sinuses and mouth, permitting speech. However, when the intrathoracic pressure during expiration is greater than about 12 cm of water, but typically at lower pressures as described below, the pressure creates enough force to lift at least the edges of diaphragm 72 above rivet 50 and allow air to flow through axial bore holes 50e and out umbrella valve 68. In this configuration, umbrella valve 68 is open and permits airflow from tracheotomy tube assembly 52 back through valve unit 40 and out the valve unit inlet. In one embodiment, umbrella valve 68 begins to open when the intrathoracic pressure during expiration reaches about 3 cm of water, more typically about 4 cm of water, and is fully open when the intrathoracic pressure reaches about 12 cm of water, more typically about 10 cm of water. In another embodiment, umbrella valve begins to open when the intrathoracic pressure during expiration reaches about 4 cm of water, and allows increasing airflow (e.g., steadily increasing airflow) through it as the intrathoracic pressure increases, until the valve is completely open at a pressure of about 12 cm of water, typically by about 10 cm of water. The valve unit of the invention thus improves comfort and allows some people to tolerate a speaking valve who could not otherwise do so because their airway is too obstructed to comfortably clear air inspired through the first valve.

Figure 7:
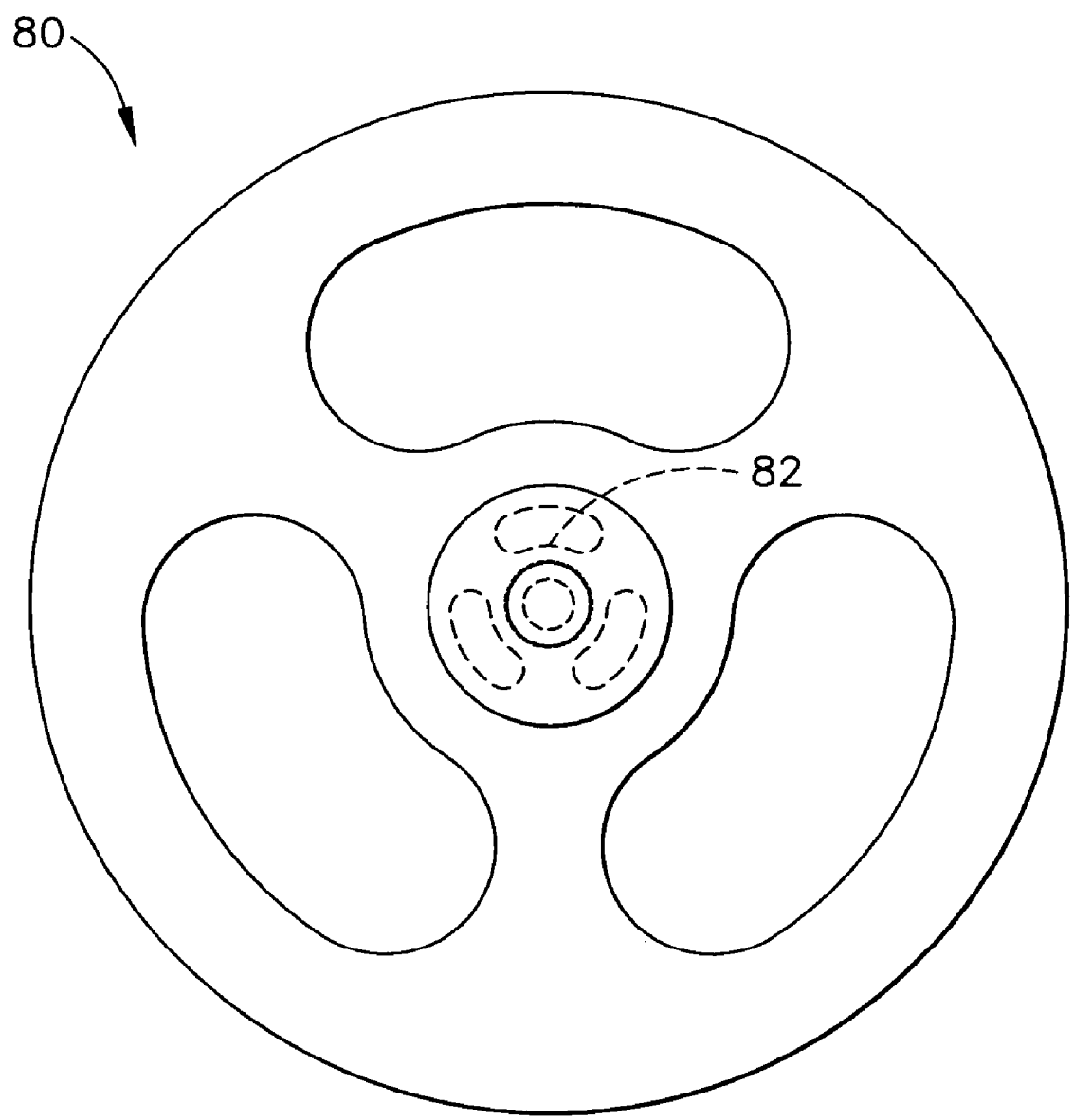
FIG. 7 is a plan view of another tracheotomy valve unit of the invention viewing the valve unit from the side toward the ambient air (i.e., external to the patient using the device).

FIG. 7 is a plan view of another valve unit 80 of the invention, viewing it from the external end of its valve base. Valve unit 80 is similar to valve unit 40 shown in FIGS. 5 and 6, except that instead of the second valve comprising six cylindrical bore holes 50e, valve unit 80 comprises three kidney-shaped bore holes 82 through which excess intrathoracic pressure is released.

Although various embodiments of the invention have been described and exemplified, the scope of the invention is not limited to that description. Changes and modifications will occur to those of ordinary skill in this art and can be made without departing from the spirit and scope of the invention. In particular, it will occur to persons skilled in the art that other means may be provided for preventing the buildup of excess pressure in the trachea during exhalation while permitting ingress of air for inhalation, whereby the desirable effects of the invention will be accomplished. The invention is considered to include the methods of accomplishing those results as well as structures designed to accomplish them.

As used herein, the term "comprising" means various components, capabilities and/or steps can be conjointly employed in the present invention. Accordingly, the term "comprising" encompasses the more restrictive terms "consisting essentially of" and "consisting of".

What is claimed is:

1. A tracheotomy valve unit adapted to cooperate with a tracheotomy tube inserted into a patient's trachea, said valve unit comprising:
   a. a first end comprising a connector adapted for connection to the free end of the tracheotomy tube and a valve base adapted to receive the connector;
   b. a second end comprising a valve unit inlet, the valve unit inlet comprising a support comprising a crosspiece configured to form air ports therethrough and a disk-shaped member defining a hole therethrough;
   c. a first valve comprising a seating ring extending inward from the support around the outer periphery of the air ports, a thin, flexible diaphragm biased against the seating ring and making positive closure contact therewith, and a rivet for connecting the diaphragm to the seating ring, the rivet adapted to sealingly fit into the hole defined by the disk-shaped member and having a length to bias the diaphragm against the seating ring, wherein the first valve permits airflow from the valve unit inlet through the valve unit and to the tube in the patient's trachea when the patient inhales, and blocks airflow from the tube through the valve unit when the patient exhales; and
   d. a second valve located in an axial bore hole of the rivet and operable to open during pressures associated with speaking, wherein the second valve begins to open to permit airflow from the tube through the valve unit and out the valve unit when the intrathoracic pressure during expiration reaches about 3 cm of water, allows increasing airflow through it as the intrathoracic pressure during expiration increases, is fully open and allows maximum airflow therethrough when the intrathoracic pressure is greater than about 12 cm of water, and blocks such airflow when the intrathoracic pressure during expiration is less than about 4 cm of water.

2. The valve unit of claim 1 wherein the diaphragm is made of low-modulus silicone sheet material.

3. The valve unit of claim 1 wherein the diaphragm is biased against the seating ring by a pressure of from about 8 to about 15 mm of water head.

4. The valve unit of claim 1 wherein the second valve comprises a slit valve or an umbrella valve.

5. The valve unit of claim 4 wherein the diaphragm is biased against the seating ring by a pressure of from about 8 to about 15 mm of water head.

6. The valve unit of claim 5 wherein the diaphragm is made of low-modulus silicone sheet material.

7. The valve unit of claim 1 wherein the second valve begins to open to permit airflow from the tube through the valve unit and out the valve unit when the intrathoracic pressure during expiration reaches about 4 cm of water, allows increasing airflow through it as the intrathoracic pressure during expiration increases, is fully open and allows maximum airflow therethrough when the intrathoracic pressure reaches about 10 cm of water, and blocks such airflow when the intrathoracic pressure during expiration is less than about 4 cm of water.

8. The valve unit of claim 7 wherein the second valve comprises a slit valve.

9. The valve unit of claim 1 wherein the second valve begins to open to permit airflow from the tube through the valve unit and out the valve unit when the intrathoracic pressure during expiration is about 4 cm of water, and is fully open when the intrathoracic pressure during expiration is about 10 cm of water.

10. The valve unit of claim 9 wherein the second valve comprises a slit valve.

11. A tracheotomy valve unit adapted to cooperate with a tracheotomy tube inserted into a patient's trachea, said valve unit comprising:
    (a) a first end adapted for connection to the free end of the tracheotomy tube;
    (b) a second end comprising a valve unit inlet, the valve unit inlet comprising a support comprising a crosspiece configured to form air ports therethrough and a disk-shaped member defining a hole therethrough;
    (c) a first valve that permits airflow from the valve unit inlet through the valve unit and to the tube in the patient's trachea when the patient inhales, and blocks airflow from the tube through the valve unit when the patient exhales, said first valve comprising a seating ring extending inward from the support around the outer periphery of the air ports, a thin, flexible diaphragm biased against the seating ring, thereby making positive closure contact therewith, and a rivet for connecting the diaphragm to the seating ring, the rivet adapted to sealingly fit into the hole defined by the disk-shaped member and having a length to bias the diaphragm against the seating ring; and
    (d) a second valve that begins to open to permit airflow from the tube through the valve unit and out the valve unit when the intrathoracic pressure during expiration reaches about 3 cm of water, is fully open when the intrathoracic pressure is greater than about 12 cm of water, and blocks such airflow when the intrathoracic pressure during expiration is less than about 4 cm of water, wherein the second valve comprises a slit valve or an umbrella valve that is located in an axial bore hole of the rivet.

12. The valve unit of claim 11 wherein the diaphragm is made of low-modulus silicone sheet material.

13. The valve unit of claim 12 wherein the second valve begins to open to permit airflow from the tube through the valve unit and out the valve unit when the intrathoracic pressure during expiration reaches about 4 cm of water, is fully open when the intrathoracic pressure reaches about 10 cm of water, and blocks such airflow when the intrathoracic pressure during expiration is less than about 4 cm of water, and wherein the second valve comprises a slit valve.

14. The valve unit of claim 12 wherein the second valve begins to open to permit airflow from the tube through the valve unit and out the valve unit when the intrathoracic pressure during expiration is about 4 cm of water, and is fully open when the intrathoracic pressure during expiration is about 10 cm of water, and wherein the second valve comprises a slit valve.

15. The valve unit of claim 14 wherein the second valve allows increasing airflow through it as the intrathoracic pressure during expiration reaches about 4 cm of water until maximum airflow is achieved at a pressure of about 10 cm of water.

\* \* \* \* \*